United States Patent
Kim et al.

(10) Patent No.: US 11,602,322 B2
(45) Date of Patent: Mar. 14, 2023

(54) ISCHEMIC STROKE DETECTION AND CLASSIFICATION METHOD BASED ON MEDICAL IMAGE, APPARATUS AND SYSTEM

(71) Applicant: Heuron Co., Ltd., Incheon (KR)

(72) Inventors: Dohyun Kim, Suwon-si (KR); Soohwa Song, Incheon (KR); Sumin Jung, Gwangju-si (KR); Jin Soo Lee, Seoul (KR); Seong Joon Lee, Seoul (KR); Seung Yon Koh, Seongnam-si (KR)

(73) Assignee: Heuron Co., Ltd., Incheon (KR)

( * ) Notice: Subject to any disclaimer, the term of this patent is extended or adjusted under 35 U.S.C. 154(b) by 0 days.

(21) Appl. No.: 17/338,803

(22) Filed: Jun. 4, 2021

(65) Prior Publication Data

US 2022/0240880 A1    Aug. 4, 2022

(30) Foreign Application Priority Data

Feb. 3, 2021 (KR) .................. 10-2021-0015166

(51) Int. Cl.
*A61B 6/00* (2006.01)
*G06T 7/62* (2017.01)
(Continued)

(52) U.S. Cl.
CPC ............ *A61B 6/5217* (2013.01); *A61B 6/501* (2013.01); *A61B 6/504* (2013.01); *A61B 6/507* (2013.01);
(Continued)

(58) Field of Classification Search
CPC ....... A61B 6/5217; A61B 6/501; A61B 6/504; A61B 6/507; G06T 7/0014; G06T 7/62;
(Continued)

(56) References Cited

U.S. PATENT DOCUMENTS

| 2018/0144467 A1* | 5/2018 | Sofka ................... G06T 7/0016 |
| 2020/0294241 A1 | 9/2020 | Wu et al. |
| 2021/0004997 A1* | 1/2021 | Manhart ............... G06T 7/0012 |

FOREIGN PATENT DOCUMENTS

| CN | 111938686 A | 11/2020 |
| JP | 2013-85652 | 5/2013 |

(Continued)

OTHER PUBLICATIONS

Lee et al., "Diagnostic and Therapeutic Strategies for Acute Intracranial Atherosclerosis-related Occlusions", Journal of Stroke, vol. 19, No. 2, May 2017, pp. 143-151 (9 pages total).
(Continued)

*Primary Examiner* — Amelie R Davis
(74) *Attorney, Agent, or Firm* — Sughrue Mion, PLLC

(57) ABSTRACT

The present disclosure relates to a method, an apparatus, and a system for detecting and classifying an ischemic stroke based on a medical image. A medical image based ischemic stroke detecting and type classifying apparatus according to an aspect of the present disclosure includes an acquiring unit which collects images related to a brain of at least one patient; a detecting unit which determines whether the at least one patient is a large vessel occlusion patient, based on the collected image; a determining unit which determines whether a type of the large vessel occlusion is embolism or intracranial atherosclerosis (ICAS), when the at least one patient is a large vessel occlusion patient; and a diagnosing unit which provides treatment direction information which is applied differently according to the determined type of the large vessel occlusion.

13 Claims, 8 Drawing Sheets

(51) Int. Cl.
 *G06T 7/70* (2017.01)
 *G06T 7/00* (2017.01)
 *G16H 50/20* (2018.01)
 *G16H 30/40* (2018.01)
 *G06N 3/04* (2023.01)

(52) U.S. Cl.
 CPC .............. *G06T 7/0014* (2013.01); *G06T 7/62* (2017.01); *G06T 7/70* (2017.01); *G16H 30/40* (2018.01); *G16H 50/20* (2018.01); *G06N 3/0445* (2013.01); *G06T 2207/20084* (2013.01); *G06T 2207/30016* (2013.01); *G06T 2207/30104* (2013.01)

(58) Field of Classification Search
 CPC .............. G06T 7/70; G06T 2207/20084; G06T 2207/30016; G06T 2207/30104; G16H 30/40; G16H 50/20; G06N 3/0445
 See application file for complete search history.

(56) References Cited

FOREIGN PATENT DOCUMENTS

| | | |
|---|---|---|
| KR | 10-1540254 B1 | 7/2015 |
| KR | 10-1754291 B1 | 7/2017 |
| KR | 10-1860566 B1 | 5/2018 |
| KR | 10-1992057 B1 | 6/2019 |
| KR | 10-2058884 B1 | 12/2019 |
| KR | 10-2068836 B1 | 2/2020 |
| KR | 10-2189622 B1 | 12/2020 |
| WO | 2008/038644 A1 | 4/2008 |
| WO | 2008/056638 A1 | 5/2008 |
| WO | 2017/160531 A1 | 9/2017 |

OTHER PUBLICATIONS

Korean Patent Office, Notice of Preliminary Rejection dated Jul. 16, 2021 in counterpart Application No. 10-2021-0015166.

Korean Patent Office, Decision for Grant of Patent dated Jul. 28, 2021 in counterpart Application No. 10-2021-0015166.

Jin Soo Lee et al., "Diagnostic and Therapeutic Strategies for Acute Intracranial Atherosclerosis-related Occlusions", Journal of Stroke, vol. 19, No. 2, pp. 143-151 (9 pages total).

Jin Soo Lee et al., "Endovascular Therapy of Cerebral Arterial Occlusions: Intracranial Atherosclerosis versus Embolism", Journal of Stroke and Cerebrovascular Diseases, 2015, vol. 24, No. 9, pp. 2074-2080 (7 pages total).

Jang-Hyun Baek et al., "Angiographical Identification of Intracranial, Atherosclerosis-Related, Large Vessel Occlusion in Endovascular Treatment", Occlusion Type for ICAS-LVO in EVT, Frontiers in Neurology, 2019, vol. 10, Article 298, pp. 1-8 ( 8 pages total).

* cited by examiner

ISCHEMIC STROKE DETECTION AND CLASSIFICATION METHOD BASED ON MEDICAL IMAGE, APPARATUS AND SYSTEM

CROSS-REFERENCE TO RELATED APPLICATIONS

This application claims the priority of Korean Patent Application No. 10-2021-0015166 filed on Feb. 3, 2021, in the Korean Intellectual Property Office, the disclosure of which is incorporated herein by reference.

BACKGROUND

Field

The present disclosure relates to a method, an apparatus, and a system for detecting and classifying an ischemic stroke based on a medical image, and more particularly, to a method, an apparatus, and a system for detecting a position of a large vessel occlusion and classifying a type of the generated large vessel occlusion based on medical images acquired from a suspected ischemic stroke patient due to the large vessel occlusion and patient information to calculate and provide information for supporting health care providers to determine a treatment direction suitable for the patient.

DESCRIPTION OF THE RELATED ART

Brain diseases, that is, cerebrovascular diseases include cerebral hemorrhage caused by bursting of cerebrovascular, cerebral infarction caused by the blockage of cerebrovascular due to blood clots, and cerebral aneurysm caused by cerebrovascular which is abnormally swollen and the cerebral hemorrhage and the cerebral infarction are called "stroke".

In order to diagnose such brain diseases, non-invasive techniques such as ultrasound diagnosis, brain CT, and brain MRI (magnetic resonance imaging) are being used.

The ultrasound diagnose method is a carotid ultrasound diagnosis which may easily invasively diagnose atherosclerotic lesions of the carotid artery. Further, transcranial Doppler test is used to measure cerebral blood flow in the cranial cavity to be applied to clinical applications.

The diagnostic method using brain CT is good for diagnosis of hemorrhagic diseases and is a recently developed technique to be very helpful in treating stroke patients (especially, ischemic patients) by capturing a cerebral blood flow state and cerebrovascular.

The diagnostic method using brain MRI is not affected by artifacts due to a skull as compared with the brain CT so that details of lesions in the brainstem, cerebellum, and temporal lobe can be diagnosed and early detection of cerebral infarction and micro diagnosis of cerebral perfusion status are possible, and the cerebrovascular condition can be thoroughly diagnosed. Therefore, it can be said that the diagnostic method using brain MRI is the best way to diagnose the condition of the brain tissue.

Specifically, the stroke is a disease which causes brain damages due to blockage or rupture of blood vessels which supply blood to the brain and thus causes physical disability. The stroke is an important cause of death worldwide and classified as a high risk disease which causes permanent disability even though it does not lead to death.

Conventionally, the stroke has been mainly regarded as a disease of the elderly. However, recently, as the stroke frequently occurs even in the thirties and forties, the stroke is recognized as a very dangerous disease which broadly occurs not only in the elderly, but also in young adults and middle-aged people.

The stroke may be classified into "ischemic stroke" caused by the blockage of blood vessel which supplies blood to the brain and "cerebral hemorrhage" caused by the bleeding by the bursting of blood vessels to the brain.

The ischemic stroke accounts for about 80% of the total strokes and most of the ischemic stroke is generated due to the blockage of the blood vessel, which supplies oxygen and nutrients to the brain, caused by thrombosis which is a coagulated blood clot.

In the ischemic stroke, the type of the large vessel occlusion may be classified into embolism and intracranial atherosclerosis (hereinafter, abbreviated as "ICAS").

First, the embolism refers to a state in which a part or all of the vascular cavity is blocked by various suspended objects carried through the blood flow, a material which causes the embolism is called embolus, and the most common embolus is thrombi created in the heart.

Next, ICAS is a disease in which the deposits of cholesterol on the innermost membrane (endothelium) of blood vessels and the growth of vascular endothelial cell cause the blood vessel to be narrowed or blocked, which causes dysfunction of blood flow to the periphery.

That is, representatively, the embolism refers to a disease which causes the dysfunction of the blood flow as at least a part of the blood vessel is blocked by thrombi and ICAS refers to a disease which causes the dysfunction of the blood flow due to the blood vessel narrowed by arteriosclerosis and in situ thrombosis.

Currently, primarily, a treatment using a thrombolytic agent which is a drug treatment agent which dissolves clots formed by the blood coagulation within three hours to four and half hours from the time when the occlusion occurs is tried or a treatment by thrombectomy within 24 hours has been approved, without identifying whether the large vessel occlusion of the patient is Embolism or ICAS.

However, in the case of the ICAS, when the treatment using the thrombolytic agent is performed, platelets are more coagulated in the body so that it is difficult to perform a treatment using antiplatelet agents for 24 hours. Therefore, there may be a problem in that the primarily performed thrombolytic treatment may deteriorate the condition.

Further, in the case of the embolism, when the thrombi are removed by the thrombectomy, the problems are solved. In contrast, in the case of the ICAS, even after removing the thrombi, stenosis due to arteriosclerosis still remains so that follow-up treatment is required. However, since two types are same, it is difficult for the health care providers to identify the type of large vessel occlusion in advance before the surgery and it is impossible to find out the corresponding situation and the necessity of the follow-up treatment after performing the treatment.

Accordingly, in order to solve the problems of the related art, it is requested to develop a method, an apparatus, and a system for supporting health care providers to determine an appropriate treatment direction matching a type of the classified occlusion by detecting a position of occluded large vessel and classifying a type of the generated large vessel occlusion with respect to suspected ischemic stroke patients due to the large vessel occlusion.

RELATED ART DOCUMENT

Patent Document

1. Korean Registered Patent No. 10-1992057 (published on Jun. 24, 2019)

2. Korean Registered Patent No. 10-1754291 (published on Jul. 6, 2017)

SUMMARY

In order to solve the above-described problems of the related art, the present disclosure is to propose a method, an apparatus, and a system for detecting and classifying ischemic stroke based on medical images.

Specifically, an object of the present disclosure is to provide a method, an apparatus, and a system for detecting a position of an occluded large vessel and classifying a cause of the generated large vessel occlusion based on medical images acquired from a suspected ischemic stroke patient due to the large vessel occlusion and patient information to calculate and provide information for supporting health care providers to determine a treatment direction suitable for the patient.

Further, an object of the present disclosure is to provide a method, an apparatus, and a system for classifying a type of the generated large vessel occlusion by determining whether an effect according to collateral circulation formation in the vicinity of the occluded large vessel is present in the medical image.

Further, an object of the present disclosure is to provide a method, an apparatus, and a system for classifying a type of the generated large vessel occlusion by identifying whether a bifurcation of the occluded blood vessel is blocked or open to identify whether a corresponding part is branching site occlusion (BSO) or truncal type occlusion (TTO) when the position of the occluded large vessel corresponds to posterior circulation (PC).

Further, an object of the present disclosure is to provide a method, an apparatus, and a system for classifying a type of the generated large vessel occlusion using information indicating that the corresponding part is branching site occlusion (BSO)/truncal type occlusion (TTO), collateral circulation formation information, and physical information of the patient together when the position of the occluded large vessel corresponds to anterior circulation (AC).

Further, an object of the present disclosure is to provide a method, an apparatus, and a system for supporting health care providers to identify a type of the large vessel occlusion before the surgery in advance and determining a treatment direction appropriate for the patient by identifying whether the type of the generated large vessel occlusion is embolism or ICAS.

In the meantime, technical objects to be achieved in the present disclosure are not limited to the aforementioned technical objects, and another not-mentioned technical object will be obviously understood by those skilled in the art from the description below.

In order to achieve the above-described technical objects, according to an aspect of the present disclosure, a medical image based ischemic stroke detecting and classifying apparatus may include: an acquiring unit which collects images related to a brain of at least one patient; a detecting unit which determines whether the at least one patient is a large vessel occlusion patient, based on the collected image; a determining unit which determines whether a type of the large vessel occlusion is embolism or intracranial atherosclerosis (ICAS), when the at least one patient is a large vessel occlusion patient; and a diagnosing unit which provides treatment direction information which is applied differently according to the determined type of the large vessel occlusion.

Further, the acquiring unit collects an angiography image related to the brain of the at least one patient and the detecting unit may determine whether the at least one patient is a large vessel occlusion patient using voxel information of the angiography image.

Further, the detecting unit may determine whether the at least one patient is a large vessel occlusion patient using an artificial intelligence model architecture which is configured by combining a recurrent neural network (RNN) layer for considering a serial slice of the at least one patient in the angiography image and a convolutional neural network (CNN) layer for extracting a feature in the angiography image.

Further, in the case of ICAS, the blood flow in the blood vessel is reduced as arteriosclerosis progresses and in order to compensate for the reduced blood flow, collateral circulation is developed in the vicinity of the blood vessel where the arteriosclerosis progresses, and when a first event in which the collateral circulation is developed is observed, the determining unit may determine the type of the large vessel occlusion as ICAS.

Further, the acquiring unit collects a perfusion image and a diffusion image related to the brain of the at least one patient and the determining unit may determine whether to observe the first event using at least one of the perfusion image and the diffusion image.

Further, when at least one of a first condition in which a difference between an infarct core volume and a volume of a surrounding cortex region is equal to or higher than a predetermined value in the perfusion image and a second condition in which the infarct pattern appears as a scattered pattern or a border zone infarct pattern in the diffusion image is satisfied, the determining unit determines that the first event is observed and may determine the type of the large vessel occlusion as ICAS.

Further, when at least one of a first condition in which a cerebral blood volume (CBV) is reduced in the perfusion image and a second condition in which the infarct pattern is a territorial infarct pattern in the diffusion image is satisfied, the determining unit determines that the first event is not observed and may determine the type of the large vessel occlusion as embolism.

Further, when the at least one patient is a large vessel occlusion patient, the determining unit determines whether a position of the large vessel occlusion corresponds to posterior circulation (PC) or anterior circulation (AC), determines whether a type of the large vessel occlusion is branching-site occlusion (BSO) or truncal-type occlusion (TTO), and may determine a type of the large vessel occlusion based on first determination for posterior circulation (PC) or anterior circulation (AC) and second determination of BSO or TTO.

Further, when the position of the large vessel occlusion is located in the posterior circulation (PC), if the type of the large vessel occlusion is the BSO, the determining unit determines the large vessel occlusion to be embolism and if the type of the large vessel occlusion is the TTO, may determine the large vessel occlusion to be ICAS.

Further, when the position of the large vessel occlusion is located in the anterior circulation (AC), the acquiring unit additionally collects physical information related to the at least one patient, in the case of ICAS, the blood flow in the blood vessel is reduced as arteriosclerosis progresses and in order to compensate for the reduced blood flow, collateral circulation is developed in the vicinity of the blood vessel where the arteriosclerosis progresses, and the determining unit determines whether a first event in which the collateral circulation is developed is observed, and may determine a type of the large vessel occlusion using the physical information, information indicating whether the first event is observed, and information indicating whether the type of the large vessel occlusion is the BSO or TTO together.

Further, when the determined type of the large vessel occlusion is the ICAS, the diagnosing unit may primarily provide a treatment using percutaneous transluminal angioplasty and/or treatment direction information using an antiplatelet agent.

Further, when an additional treatment is necessary for the at least one patient, the diagnosing unit may secondarily provide at least one of a treatment using a thrombolytic agent, a treatment using thrombectomy, a treatment using a drug other than the antiplatelet agent, a treatment using a stent, a treatment using insertion of balloon, and/or counterpulsation treatment direction information.

Further, when the treatment using thrombectomy is applied to the at least one patient, if a predetermined time elapses, information proposing to stop the treatment using thrombectomy may be provided.

Further, when the determined type of the large vessel occlusion is the embolism, the diagnosing unit determines whether the at least one patient is a mild patient or a serious patient, provides treatment direction information using a thrombolytic agent for the mild patient, and may provide treatment direction information using thrombectomy for the serious patient.

Further, the apparatus may further include a communication unit which the treatment direction information provided by the diagnosing unit to a predetermined institution based on wired and/or wireless communication.

In the meantime, in order to achieve the above-described technical objects, according to another aspect of the present disclosure, a medical image based ischemic stroke detecting and classifying method may include a first step of collecting images related to a brain of at least one patient, by an acquiring unit; a second step of determining whether the at least one patient is a large vessel occlusion patient, based on the collected image by a detecting unit; a third step of determining whether a type of the large vessel occlusion is embolism or intracranial atherosclerosis (ICAS), when the at least one patient is a large vessel occlusion patient by a determining unit; and a fourth step of providing treatment direction information which varies depending on the determined type of the large vessel occlusion by a diagnosing unit.

Further, in the first step, the acquiring unit collects an angiography image related to the brain of the at least one patient, and in the second step, the detecting unit may determine whether the at least one patient is a large vessel occlusion patient using voxel information of the angiography image.

Further, in the second step, the detecting unit may determine whether the at least one patient is a large vessel occlusion patient using an artificial intelligence model architecture which is configured by combining a recurrent neural network (RNN) layer for considering a serial slice of the at least one patient in the angiography image and a convolutional neural network (CNN) layer for extracting a feature in the angiography image.

Further, in the case of ICAS, the blood flow in the blood vessel is reduced as arteriosclerosis progresses and in order to compensate for the reduced blood flow, collateral circulation is developed in the vicinity of the blood vessel where the arteriosclerosis progresses, and in the third step, when a first event in which the collateral circulation is developed is observed, the determining unit determines the type of the large vessel occlusion as ICAS.

Further, in the first step, the acquiring unit collects a perfusion image and a diffusion image related to the brain of the at least one patient and in the third step, the determining unit may determine whether to observe the first event using at least one of the perfusion image and the diffusion image.

Further, when at least one of a first condition in which a difference between an infarct core volume and a volume of a surrounding cortex region is equal to or higher than a predetermined value in the perfusion image and a second condition in which the infarct pattern appears as a scattered pattern or a border zone infarct pattern in the diffusion image is satisfied, in the third step, the determining unit determines that the first event is observed and may determine the type of the large vessel occlusion as ICAS.

Further, when at least one of a first condition in which a cerebral blood volume (CBV) is reduced in the perfusion image and a second condition in which the infarct pattern is a territorial infarct pattern in the diffusion image is satisfied, in the third step, the determining unit determines that the first event is not observed and may determine the type of the large vessel occlusion as embolism.

Further, the third step may include: a step 3-1 of when the at least one patient is a large vessel occlusion patient, determining whether a position of the large vessel occlusion corresponds to posterior circulation (PC) or anterior circulation (AC) by the determining unit; a step 3-2 of determining whether a type of the large vessel occlusion is branching-site occlusion or truncal-type occlusion by the determining unit, and a step 3-3 of determining a type of the large vessel occlusion based on first determination for posterior circulation (PC) or anterior circulation (AC) and second determination of BSO or TTO, by the determining unit.

Further, when the position of the large vessel occlusion is located in the posterior circulation (PC), in the step 3-3, if the type of the large vessel occlusion is the BSO, the determining unit determines the large vessel occlusion to be embolism and if the type of the large vessel occlusion is the TTO, may determine the large vessel occlusion to be ICAS.

Further, when the position of the large vessel occlusion is located in the anterior circulation (AC), in the first step, the acquiring unit additionally collects physical information related to the at least one patient, in the case of ICAS, the blood flow in the blood vessel is reduced as arteriosclerosis progresses and in order to compensate for the reduced blood flow, collateral circulation is developed in the vicinity of the blood vessel where the arteriosclerosis progresses, and in the step 3-2, the determining unit determines whether a first event in which the collateral circulation is developed is observed, in the step 3-3, the determining unit may determine a type of the large vessel occlusion using the physical information, information indicating whether the first event is observed, and information indicating whether the type of the large vessel occlusion is the BSO or TTO together.

Further, when the determined type of the large vessel occlusion is the ICAS, the fourth step may include a step 4-1 of primarily providing treatment using percutaneous transluminal angioplasty and/or treatment direction information using an antiplatelet agent by the diagnosing unit; and a step 4-2 of, when an additional treatment is necessary for the at least one patient, secondarily providing at least one of a treatment using a thrombolytic agent, a treatment using thrombectomy, a treatment using a drug other than the antiplatelet agent, a treatment using a stent, a treatment using insertion of balloon, and/or counterpulsation treatment direction information, by the diagnosing unit.

Further, the fourth step may further include a step 4-3 of, when the treatment using thrombectomy is applied to the at least one patient in the step 4-2, if a predetermined time elapses, providing information proposing to stop the treatment using thrombectomy.

Further, when the determined type of the large vessel occlusion is the embolism, the fourth step may include a step 4-1 of determining whether the at least one patient is a mild patient or a serious patient, by the diagnosing unit; and a step 4-2 of providing treatment direction information using a thrombolytic agent for the mild patient and providing treatment direction information using thrombectomy for the serious patient.

Further, after the fourth step, the method may further include a fifth step of transmitting the treatment direction information provided by the diagnosing unit to a predetermined institution based on wired and/or wireless communication by a communication unit.

The present disclosure provides a method, an apparatus, and a system for detecting and classifying ischemic stroke based on medical images to solve the above-described problems of the related art.

Specifically, the present disclosure may provide a method, an apparatus, and a system for detecting a position of an occluded large vessel and classifying a type of the generated large vessel occlusion based on medical images acquired from a suspected ischemic stroke patient due to the large vessel occlusion and patient information to calculate and provide information for supporting health care providers to determine a treatment direction suitable for a patient.

Further, the present disclosure may provide a method, an apparatus, and a system for classifying a type of the generated large vessel occlusion by determining whether an effect according to collateral circulation formation in the vicinity of the occluded large vessel is present in the medical image.

Further, the present disclosure may provide a method, an apparatus, and a system for classifying a type of the generated large vessel occlusion by identifying whether a corresponding part is branching site occlusion (BSO) or truncal type occlusion (TTO) when the position of the occluded large vessel corresponds to posterior circulation (PC).

Further, the present disclosure may provide a method, an apparatus, and a system for classifying a type of the generated large vessel occlusion using information indicating that the corresponding part is branching site occlusion (BSO)/truncal type occlusion (TTO), collateral circulation formation information, and physical information of the patient together when the position of the occluded large vessel corresponds to anterior circulation (AC).

Further, the present disclosure may provide a method, an apparatus, and a system for supporting health care providers to identify a type of the large vessel occlusion before the surgery in advance and determining a treatment direction appropriate for the patient by identifying whether the type of the generated large vessel occlusion is embolism or ICAS.

In the meantime, a technical object to be achieved in the present disclosure is not limited to the aforementioned effects, and another not-mentioned effects will be obviously understood by those skilled in the art from the description below.

BRIEF DESCRIPTION OF DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

Hereinafter, an exemplary embodiment of the present disclosure will be described with reference to the accompanying drawings. The exemplary embodiments which will be described below do not unduly limit the contents of the present disclosure as set forth in the claims and the entire configuration described in the present embodiment cannot be said to be essential as a solution for the present disclosure.

Hereinafter, a method, an apparatus, and a system for detecting ischemic stroke and classifying a type thereof based on medical images according to an exemplary embodiment of the preset disclosure will be described in detail with reference to the accompanying drawings.

Medical Image Based Ischemic Stroke Detecting and Classifying Apparatus

Figure 1:
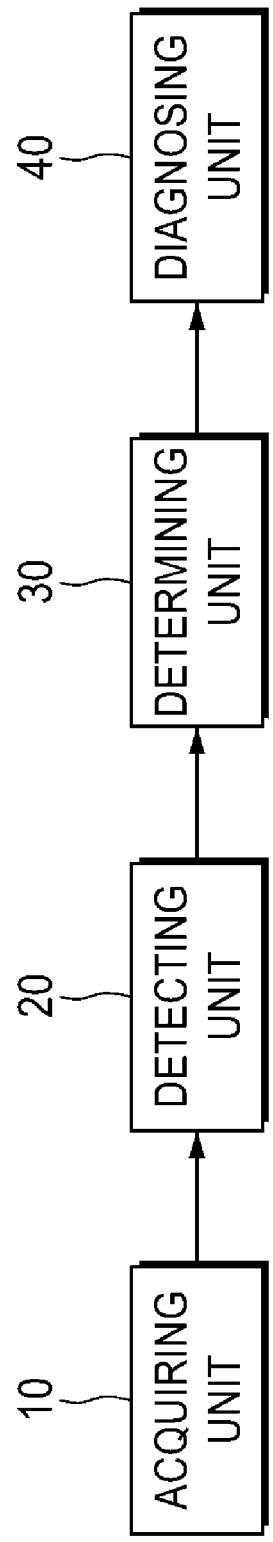
FIG. 1 illustrates an example of a block diagram of an apparatus for detecting and classifying ischemic stroke based on medical images, according to the present disclosure.

FIG. 1 illustrates an example of a block diagram of an apparatus for detecting and classifying ischemic stroke based on medical images, according to the present disclosure.

A medical image based ischemic stroke detecting and classifying apparatus 1 according to the present disclosure may include an acquiring unit 10, a detecting unit 20, a determining unit 30, and a diagnosis unit 40.

First, the acquiring unit 10 is a device which photographs a brain of a subject to be diagnosed to acquire medical images.

Further, the acquiring unit 10 according to the present disclosure may also acquire physical information with regard to the patient.

First, the acquiring unit 10 may acquire images from imaging equipment which captures various medical images such as brain CT or MRI. Images collected by the acquiring unit 10 may include contrast enhanced computed tomography (CECT), magnetic resonance image (MRI), and the like.

Specifically, the acquiring unit 10 may collect DICOM information, angiography image information, perfusion image information, and diffusion image information with regard to the patient.

More, the acquiring unit 10 according to the present disclosure may also acquire physical information with regard to the patient, such as gender or age information, blood pressure information, and onset time information.

Next, the detecting unit 20 performs image processing, determines whether ischemia is present in the brain of a patient, based on image information collected by the acquiring unit 10, and if ischemia is present, determines whether the patient has large vessel occlusion.

When the detecting unit 20 determines whether the patient is a large vessel occlusion patient, the detecting unit 20 may use voxel information of brain angiography image data collected by the acquiring unit 10.

Further, the detecting unit 20 may use an artificial intelligence model architecture to detect a large vessel occlusion (LVO) region from a 2D or 3D angiography image.

Next, when the large vessel occlusion (LVO) region is detected, the determining unit 30 determines whether the corresponding large vessel occlusion is embolism or ICAS.

At this time, the determining unit 30 determines whether it is embolism or ICAS using whether effect in accordance with collateral circulation formation is present in the image.

Further, when the position of the occluded large vessel corresponds to posterior circulation (PC), the determining unit 30 may classify a type of the generated large vessel occlusion by identifying whether a corresponding part is branching site occlusion (BSO) or truncal type occlusion (TTO).

Further, when the position of the occluded large vessel corresponds to anterior circulation (AC), the determining unit 30 may classify the type of generated large vessel occlusion using BSO/TTO information, collateral circulation formation information, and physical information of the patient together.

Next, the diagnosing unit 40 may provide information for supporting health care providers to determine a treatment direction appropriate for the patient differently in a case in which the type of the generated large vessel occlusion is embolism and a case in which the type of the generated large vessel occlusion is ICAS.

Figure 2:
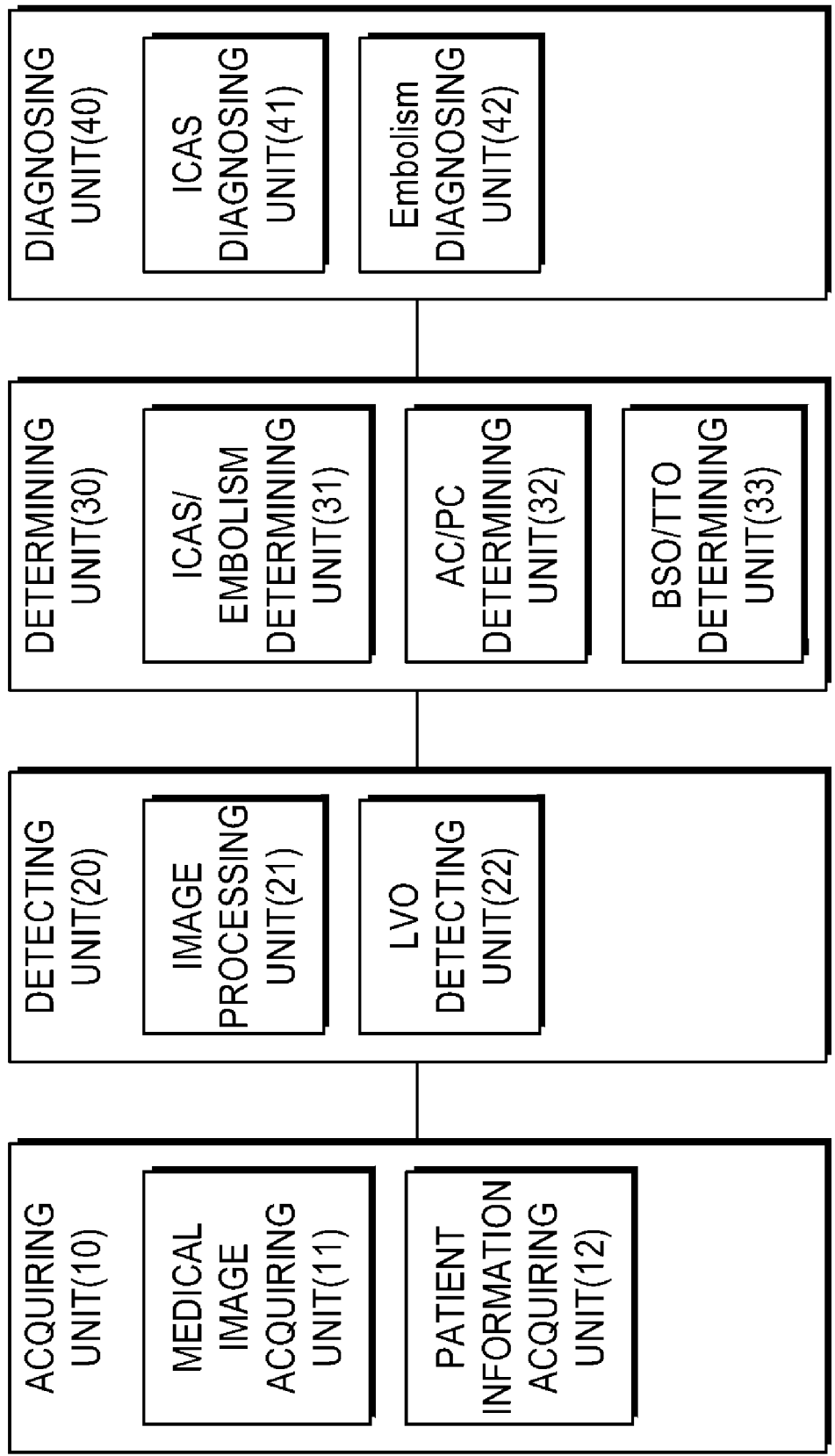
FIG. 2 illustrates an example of a block diagram including detailed configurations of an apparatus for detecting and classifying ischemic stroke based on medical images illustrated in FIG. 1.

FIG. 2 illustrates an example of a block diagram including detailed configurations of an apparatus for detecting and classifying ischemic stroke based on medical images illustrated in FIG. 1.

Referring to FIG. 2, the acquiring unit 10 may include a medical image acquiring unit 11 and a patient information acquiring unit 12.

The medical image acquiring unit 11 acquires images from imaging equipment which captures various medical images such as a brain CT or MRI and may collect contrast-enhanced computed tomography (CECT), magnetic resonance image (MRI), or the like.

As described above, the medical image acquiring unit 11 may collect DICOM information, angiography image information, perfusion image information, and diffusion image information with regard to the suspected ischemic stroke patient.

Further, the patient information acquiring unit 12 may also acquire physical information with regard to the patient, such as information such as gender or age of the suspected ischemic stroke patient, blood pressure information, and onset time information.

When the position of the occluded large vessel corresponds to posterior circulation (PC), the physical information acquired by the patient information acquiring unit 12 may be used to determine whether it is embolism or ICAS.

Next, the detecting unit 20 may include an image processing unit 21 and an LVO detecting unit 22.

First, the image processing unit 21 may provide a function such as preprocessing or image processing.

The image processing unit 21 may distinguish no hemorrhage from hemorrhage according to an artificial intelligence algorithm, based on the acquired image, normalize the preprocessed medical image, and divide and extract a region of interest using a standard mask template which is set in advance.

The image processing unit 21 may perform an operation of removing a noise from the image collected by the acquiring unit 10.

Further, the image processing unit 21 may provide a co-registration function. The co-registration function is performed to align images for alignment of an anatomical structure and spatially align images in an object or between objects in accordance with inclination due to the movement of the subject during the imaging process or a difference in a brain shape.

Further, the image processing unit 21 may further provide a skull stripping function to remove a portion other than a brain structure from the image.

Further, the image processing unit 21 may learn or classify a hemorrhage type based on artificial intelligence (AI).

Further, the image processing unit 21 normalizes the preprocessed medical image and may divide and extract a region of interest using a standard mask template which is set in advance.

The image processing unit 21 may set a standard mask template for dividing and extracting the region of interest from the medical image.

For example, the image processing unit 21 collects a plurality of medical images acquired from a plurality of normal person and brain disease patients, generates two-dimensional and three-dimensional normalization images, slices three-dimensional normalization images with respect to a specific axis according to a voxel setting to generate a two-dimensional normalization image.

Further, the image processing unit 21 may provide a function of normalizing a medical image of a subject to be diagnosed.

For example, the image processing unit 21 may normalize the image by means of processes of correcting an original medical image of the subject to be diagnosed with non-uniform bias, perform co-registration by spatial alignment, and applies a standard stereotaxic space to perform spatial normalization.

Further, the image processing unit 21 may provide a function of dividing and extracting a region of interest by applying a standard mask template to a normalized medical image.

In the meantime, when a patient with no hemorrhage has ischemia, the LVO detecting unit 22 may determine whether the patient is a large vessel occlusion patient.

The LVO detecting unit 22 receives the region of interest which is divided and extracted by applying the standard mask template to the normalized medical image to determine whether the patient with no hemorrhage has ischemia.

If a patient with no hemorrhage has ischemia, the LVO detecting unit 22 may determine whether the patient is a large vessel occlusion patient.

When there is ischemia, the LVO detecting unit 22 may determine whether the patient is a large vessel occlusion (LVO) patient using voxel information of brain angiography image data.

Further, the LVO detecting unit 22 may use an artificial intelligence model architecture to detect an LVO region from a 2D or 3D angiography image.

Here, the model architecture may be configured to combine a recurrent neural network (RNN) layer for considering a serial slice of the patient and a convolutional neural network (CNN) layer for extracting a feature.

Further, the LVO detecting unit 22 may calculate outputs for whether it is LVO, a position of LVO, and LVO type classification from CTA images of each patient.

The output calculated herein may include 3D cerebral artery reconstruction, a standard 3D Atlas of cerebral artery, co-registration, and the like.

More, the information indicating whether the patient with ischemia is a large vessel occlusion patient, and a position and a shape of the LVO may also be calculated.

In the meantime, the determining unit 30 includes an ICAS/embolism determining unit 31, an anterior circulation (AC)/posterior circulation (PC) determining unit 32, and branching site occlusion (BSO)/truncal type occlusion (TTO) determining unit 33.

First, when the large vessel occlusion (LVO) region is detected by the detecting unit 20, the ICAS/embolism determining unit 31 provides a function of determining whether the large vessel occlusion is embolism or ICAS.

At this time, the ICAS/embolism determining unit 31 according to the present disclosure determines whether the occlusion is embolism or ICAS using whether effect in accordance with collateral circulation formation is present in the image.

Representatively, the ICAS/embolism determining unit 31 according to the present disclosure may distinguish embolism from ICAS based on perfusion image information and diffusion image information.

In the case of ICAS, the blood vessel is blocked as arteriosclerosis progresses so that the blood flow is reduced and in order to compensate for this, collateral circulation in the vicinity of the blood vessel where the corresponding arteriosclerosis progresses is developed.

Accordingly, in the case of ICAS, an infarct pattern appears as a scattered pattern or a border zone infarct pattern in the diffusion image, and in the perfusion image, a contrast between the infarct core volume and a volume of a surrounding cortex area has a very large difference which is equal to or larger than a predetermined value.

That is, the ICAS/embolism determining unit 31 may determine ICAS using a fact that the effect according to the collateral circulation formation is present in the image.

Further, the embolism is a state in which a normal blood vessel is blocked by blood clots so that collateral circulation in the vicinity of position of the embolism is not developed.

Accordingly, in the case of the embolism, the territorial infarct pattern is observed from the diffusion image and a reduced pattern of the cerebral blood volume (CBV) is observed in the perfusion image.

That is, the ICAS/embolism determining unit 31 may determine embolism using a fact that the effect according to the collateral circulation formation is not present in the image.

The ICAS/embolism determining unit 31 applies an artificial intelligence classification model to configure a 3D convolutional neural network (CNN) architecture with inception-V1 as a base network, learn a feature for voxel data of brain diffusion image and the perfusion image, and classify the cause of the large vessel occlusion (LVO) in detail based thereon.

Further, when the position of the occluded large vessel corresponds to posterior circulation (PC), the ICAS/Embolism determining unit 31 may classify a type of the generated large vessel occlusion by identifying whether a corresponding part is branching site occlusion (BSO) or truncal type occlusion (TTO).

Accordingly, the AC/PC determining unit 32 may determine whether the position of the occluded large vessel corresponds to posterior circulation (PC) or an anterior circulation (AC).

Further, the BSO/TTO determining unit 33 may provide a function of determining whether the corresponding portion is branching site occlusion (BSO) or truncal type occlusion (TTO).

Further, when the position of the occluded large vessel corresponds to anterior circulation (AC), the ICAS/Embolism determining unit 31 may classify the type of generated large vessel occlusion using BSO/TTO information, collateral circulation formation information, and physical information of the patient together.

In the meantime, the diagnosing unit 40 may include an ICAS diagnosing unit 41 and an embolism diagnosing unit 42.

The diagnosing unit 40 may provide information for supporting health care providers to determine a treatment direction appropriate for the patient differently in a case in which the type of the generated large vessel occlusion is embolism and a case in which the type of the generated large vessel occlusion is ICAS.

When the type of the generated large vessel occlusion is embolism, the embolism diagnosing unit 42 determines whether a state of the patient is mild or serious.

In the case of a mild patient, the embolism diagnosing unit 42 may recommend a treatment direction using a thrombolytic agent to the health care provider.

Further, in the case of a serious patient, the embolism diagnosing unit 42 may recommend a treatment direction using a thrombectomy to the health care provider.

In the meantime, when the type of the generated large vessel occlusion is ICAS, unlike the embolism diagnosing unit 42, the ICAS diagnosing unit 41 may primarily recommend a treatment using percutaneous transluminal angioplasty and/or a treatment direction using an antiplatelet agent to the health care provider.

When such a primary treatment does not show a great effect, the ICAS diagnosing unit 41 may secondarily recommend a treatment using a thrombolytic agent and/or a treatment direction using a thrombectomy to the health care provider.

Currently, primarily, a treatment using a thrombolytic agent which is a drug treatment agent which dissolves clots formed by the blood coagulation is tried or a treatment by thrombectomy is performed, within three hours to four and half hours from the time when the occlusion occurs, without identifying whether the large vessel occlusion of the patient is Embolism or ICAS. However, in the case of the ICAS, when the treatment using the thrombolytic agent is performed, platelets are more coagulated in the body so that it is difficult to perform a treatment using antiplatelet agents for hours. Therefore, there may be a problem in that the primarily performed thrombolytic treatment may deteriorate the condition.

Further, in the case of the embolism, when the blood clots are removed by the thrombectomy, the problems are solved. In contrast, in the case of the ICAS, even after removing the blood clots, stenosis due to arteriosclerosis still remains so that follow-up treatment is required. However, it is difficult for the health care providers to identify the form of large vessel occlusion in advance before the surgery and it is impossible to find out the corresponding situation and the necessity of the follow-up treatment after performing the surgery.

Accordingly, the ICAS diagnosing unit 41 and the embolism diagnosing unit 42 provide information for supporting the health care provider to determine a treatment direction appropriate for the patient differently in a case in which the type of the generated large vessel occlusion is embolism and a case in which the type of the generated large vessel occlusion is ICAS to solve the above-mentioned problems.

Specifically, the problems of the related art may be efficiently solved based on a method, an apparatus, and a system for supporting health care providers to determine an appropriate treatment direction matching a type of the classified occlusion by detecting a position of occluded large vessel and classifying a type of the generated large vessel occlusion with respect to suspected ischemic stroke patients due to the large vessel occlusion.

Further, the information provided by the diagnosing unit 40 may be transmitted to external institution such as a hospital related to the patient, based on wired/wireless communication.

Even though it is not illustrated, information transmission to the external institution (a tertiary referral hospital) may be performed by a communication unit and the communication unit may transmit corresponding information to a predetermined outside (for example, a hospital) by wired communication, short range communication, or long-distance communication.

As the long-distance communication technique used herein, wireless LAN (WLAN) (Wi-Fi), wireless broadband (Wibro)), world interoperability for microwave access (Wimax), high speed downlink packet access (HSDPA), and the like may be used.

Further, as a short range communication technology, a Bluetooth, a radio frequency identification (RFID), an infrared data association (IrDA), an ultra-wideband (UWB), a ZigBee, and the like may be used.

Medical Image Based Ischemic Stroke Detecting and Classifying Method

Figure 3:
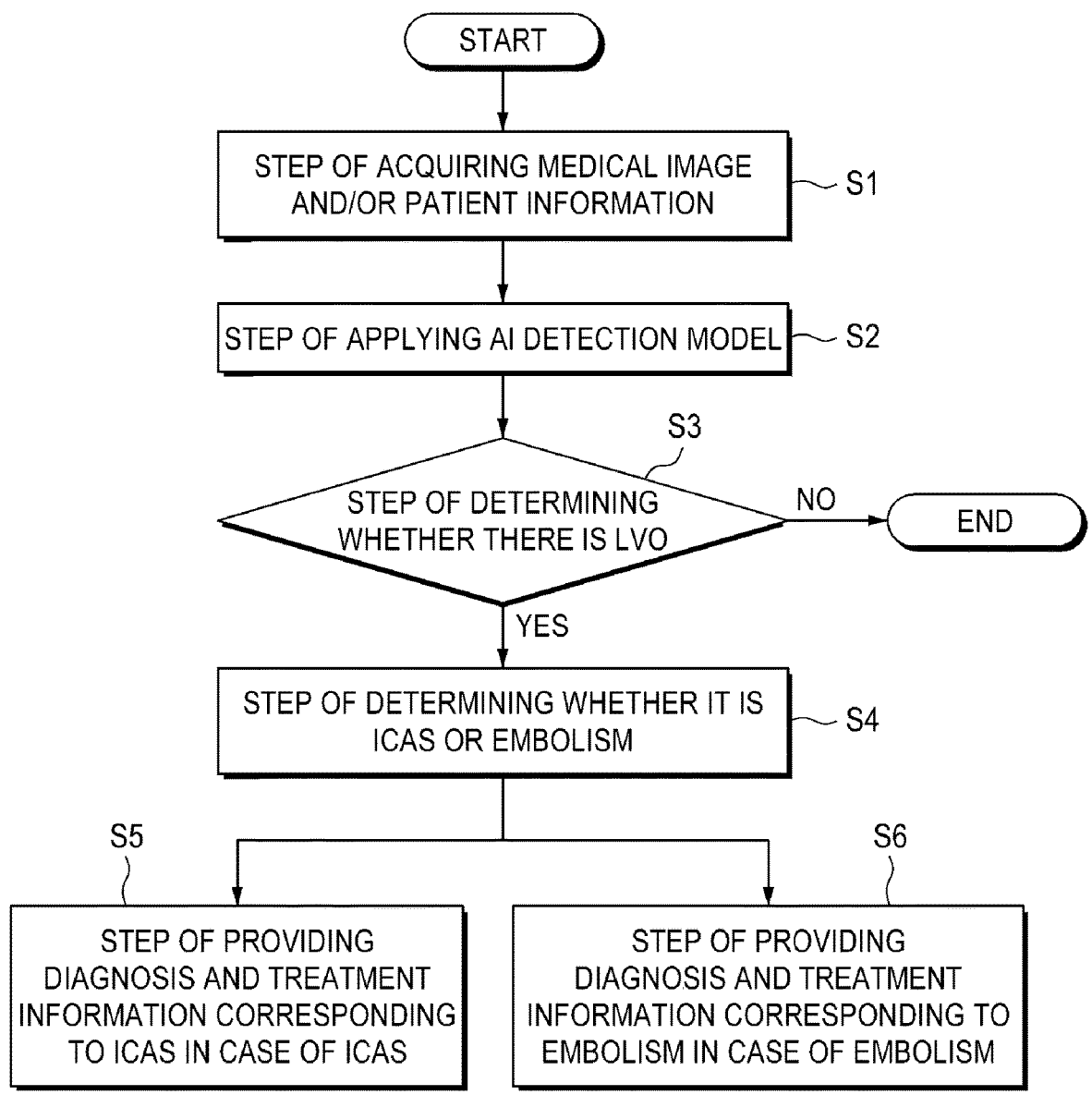
FIG. 3 illustrates an example of a flowchart for explaining an entire process of a method for detecting and classifying ischemic stroke based on medical images, proposed by the present disclosure.

FIG. 3 illustrates an example of a flowchart for explaining an entire process of a method for detecting and classifying ischemic stroke based on medical images, proposed by the present disclosure.

Referring to FIG. 3, first, the acquiring unit 10 performs a step S1 of acquiring a medical image obtained by capturing a brain of a target to be diagnosed and physical information related to a patient.

In the step S1, the medical image acquiring unit 11 of the acquiring unit 10 acquires images from imaging equipment which captures various medical images such as brain CT or MRI and may collect a contrast-enhanced computed tomography (CECT) or magnetic resonance image (MRI) and DICOM information, angiography image information, perfusion image information, and diffusion image information related to a suspected ischemic stroke patient.

Further, in the step S1, the patient information acquiring unit 12 of the acquiring unit 10 may also acquire physical information with regard to the patient, such as information such as gender or age of the suspected ischemic stroke patient, blood pressure information, and onset time information. When the position of the occluded large vessel corresponds to posterior circulation (PC), the physical information acquired herein may be used to determine whether it is embolism or ICAS.

Next, the image processing unit 21 of the detecting unit 20 performs a process of applying an AI detecting model (S2) and determining whether the patient is a large vessel occlusion patient (S3).

In the steps S2 and S3, if a patient with no hemorrhage has ischemia, the LVO detecting unit 22 may determine whether the patient is a large vessel occlusion patient based on artificial intelligence.

In the steps S2 and S3, when there is ischemia, the LVO detecting unit 22 may determine whether the patient is a large vessel occlusion (LVO) patient using voxel information of brain angiography image data.

Further, the LVO detecting unit 22 may use an artificial intelligence model architecture to detect an LVO region from a 2D or 3D angiography image.

Here, the model architecture may be configured to combine a recurrent neural network (RNN) layer for considering a serial slice of the patient and a convolutional neural network (CNN) layer for extracting a feature.

Further, in the steps S2 and S3, the LVO detecting unit 22 may calculate outputs for whether it is LVO, a position of LVO, and LVO type classification from CTA images of each patient. The output calculated herein may include 3D cerebral artery reconstruction, a standard 3D Atlas of cerebral artery, co-registration, and the like.

More, the information indicating whether the patient with ischemia is a large vessel occlusion patient, and a position and a shape of the LVO may also be calculated.

When it is determined to be the large vessel occlusion patient, after the step S3, a step S4 of determining whether the corresponding large vessel occlusion is embolism or ICAS by the ICAS/embolism determining unit 31 is performed.

In the step S4, the ICAS/embolism determining unit 31 determines whether the occlusion is embolism or ICAS using whether effect in accordance with collateral circulation formation is present in the image.

Further, when the position of the occluded large vessel corresponds to posterior circulation (PC), the ICAS/Embolism determining unit 31 may classify a type of the generated large vessel occlusion by determining whether a corresponding part is branching site occlusion (BSO) or truncal type occlusion (TTO).

Further, when the position of the occluded large vessel corresponds to anterior circulation (AC), the ICAS/Embolism determining unit 31 may classify the type of generated large vessel occlusion using BSO/TTO information, collateral circulation formation information, and physical information of the patient together.

After the step S4, the diagnosing unit 40 may provide information for supporting health care providers to determine a treatment direction appropriate for the patient differently in a case in which the type of the generated large vessel occlusion is embolism and a case in which the type of the generated large vessel occlusion is ICAS.

Specifically, when the type of the generated large vessel occlusion is ICAS, the ICAS diagnosing unit 41 may provide diagnosis and treatment information corresponding to ICAS to the health care provider (S5).

Further, when the type of the generated large vessel occlusion is embolism, the embolism diagnosing unit 42 may provide diagnosis and treatment information corresponding to embolism to the health care provider (S6).

In the meantime, even though it is not illustrated, after the step S5 and/or the step S6, the information provided by the diagnosing unit 40 may be transmitted to external institution such as a hospital related to the patient, based on wired/wireless communication.

Even though it is not illustrated, information transmission to the external institution (a tertiary referral hospital) may be performed by a communication unit and the communication unit may transmit corresponding information to a predetermined outside (for example, a hospital) by wired communication, short-distance communication, or long-distance communication.

Hereinafter, a method for identifying whether the occlusion is embolism or ICAS by the ICAS/embolism determining unit 31, with regard to the step S4 and a method of supporting to determine a treatment direction by the diagnosing unit 40 differently in a case in which the type of the large vessel occlusion is embolism and a case in which the type of the large vessel occlusion is ICAS, with regard to the steps S5 and S6 will be described in more detail with reference to the drawings.

Figure 4:
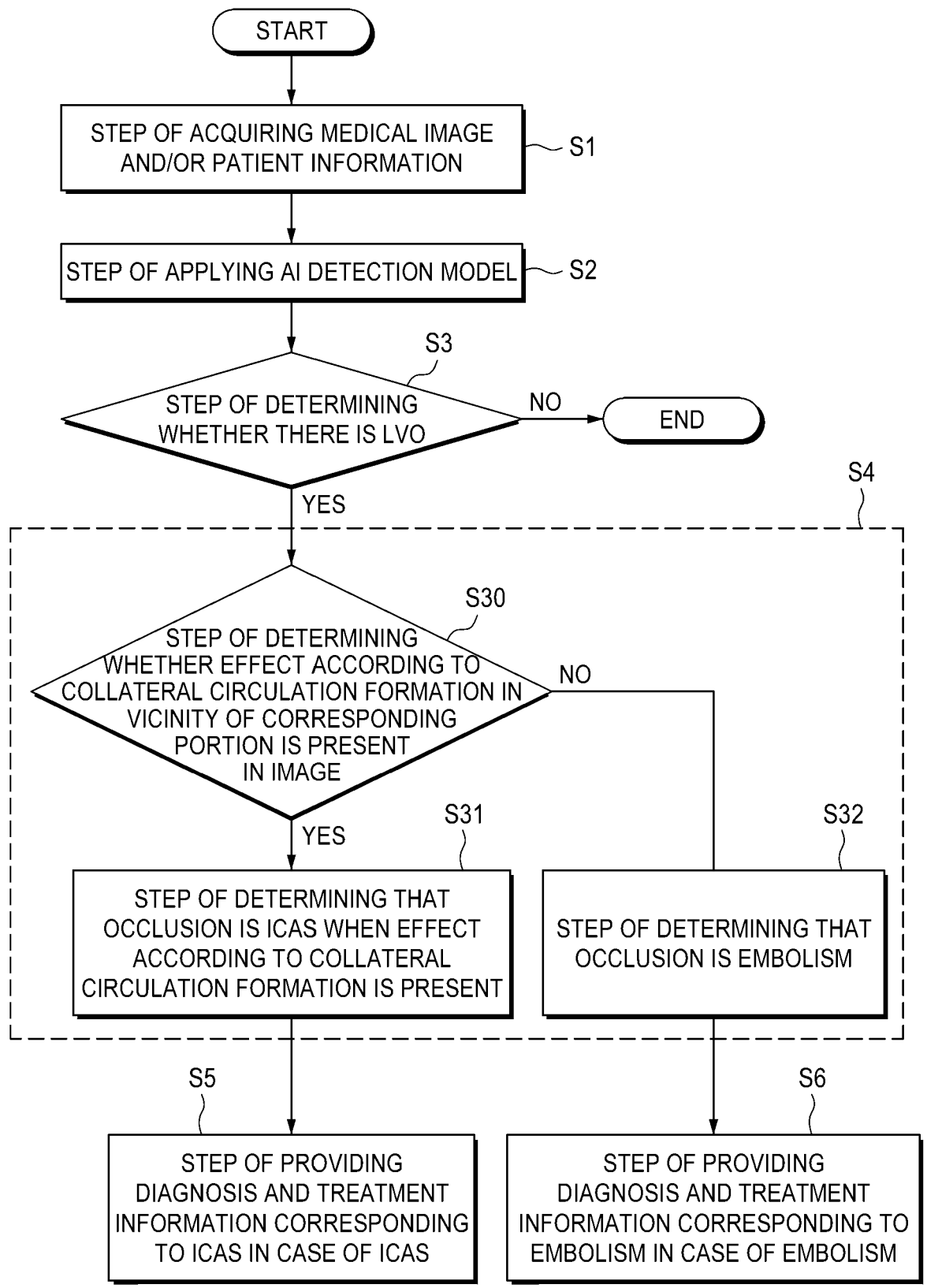
FIG. 4 illustrates a flowchart of a method using whether effect according to collateral circulation formation is present in an image, with regard to a process of classifying a type of large vessel occlusion into embolism or ICAS.

Method for Classifying Type of Large Vessel Occlusion into Embolism or ICAS Using Whether Effect According to Collateral Circulation Formation is Present in Image FIG. 4 illustrates a flowchart of a method using whether effect according to collateral circulation formation is present in an image, with regard to a process of classifying a type of large vessel occlusion into embolism or ICAS.

Referring to FIG. 4, after the step S3, when there is LVO, the ICAS/embolism determining unit 31 may determine whether effect according to collateral circulation formation is present in an image.

In the case of ICAS, the blood vessel is blocked as arteriosclerosis progresses so that the blood flow is reduced and in order to compensate for this, collateral circulation in the vicinity of the blood vessel where the corresponding arteriosclerosis progresses is developed.

Accordingly, the ICAS/embolism determining unit 31 may determine ICAS using a fact that the effect according to the collateral circulation formation is present in the image (S31).

Figure 5:
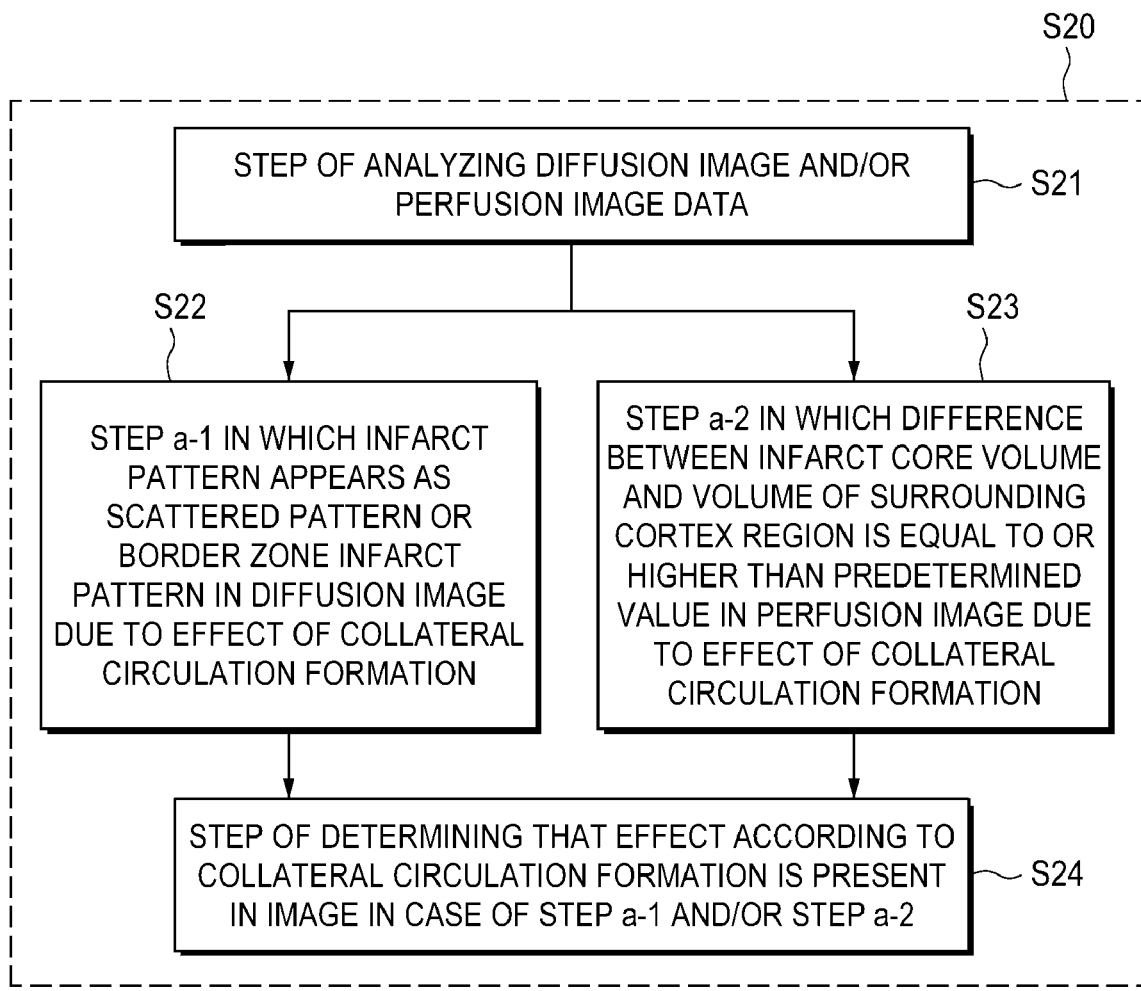
FIG. 5 is a flowchart for explaining a process of classifying a type of occlusion to ICAS because the effect according to collateral circulation formation in the vicinity of the occluded large vessel is present in a medical image, with regard to FIG. 4.

FIG. 5 is a flowchart for explaining a process of classifying a type of occlusion to ICAS because the effect according to collateral circulation formation in the vicinity of the occluded large vessel is present in a medical image, with regard to FIG. 4.

Referring to FIG. 5, the ICAS/embolism determining unit 31 may distinguish embolism from ICAS based on perfusion image information and diffusion image information.

As described above, in the case of ICAS, the blood vessel is blocked as arteriosclerosis is progressed so that the blood flow is reduced and in order to compensate for this, collateral circulation in the vicinity of the blood vessel where the arteriosclerosis is progressed is developed. In the diffusion image, a step a-1 in which the infarct pattern appears as a scattered pattern or a border zone infarct pattern may be observed (S22).

Further, in the perfusion image, a step a-2 in which a contrast between the infarct core volume and a volume of a surrounding cortex area has a very large difference which is equal to or larger than a predetermined value may be observed (S23).

When the step a-1 in which the infarct pattern appears as a scattered pattern or a border zone infarct pattern in the diffusion image and/or the step a-2 in which a contrast between the infarct core volume and a volume of a surrounding cortex area has a very large difference which is equal to or larger than a predetermined value are observed in the perfusion image, the ICAS/embolism determining unit 31 determines that the effect according to the collateral circulation formation is present in the image (S24) and may determine ICAS based thereon (S31).

Further, the embolism is a state in which a normal blood vessel is blocked by blood clots so that collateral circulation in the vicinity of position of the embolism is not developed.

Accordingly, the ICAS/embolism determining unit 31 may determine embolism using a fact that the effect according to the collateral circulation formation is not present in the image (S32).

Figure 6:
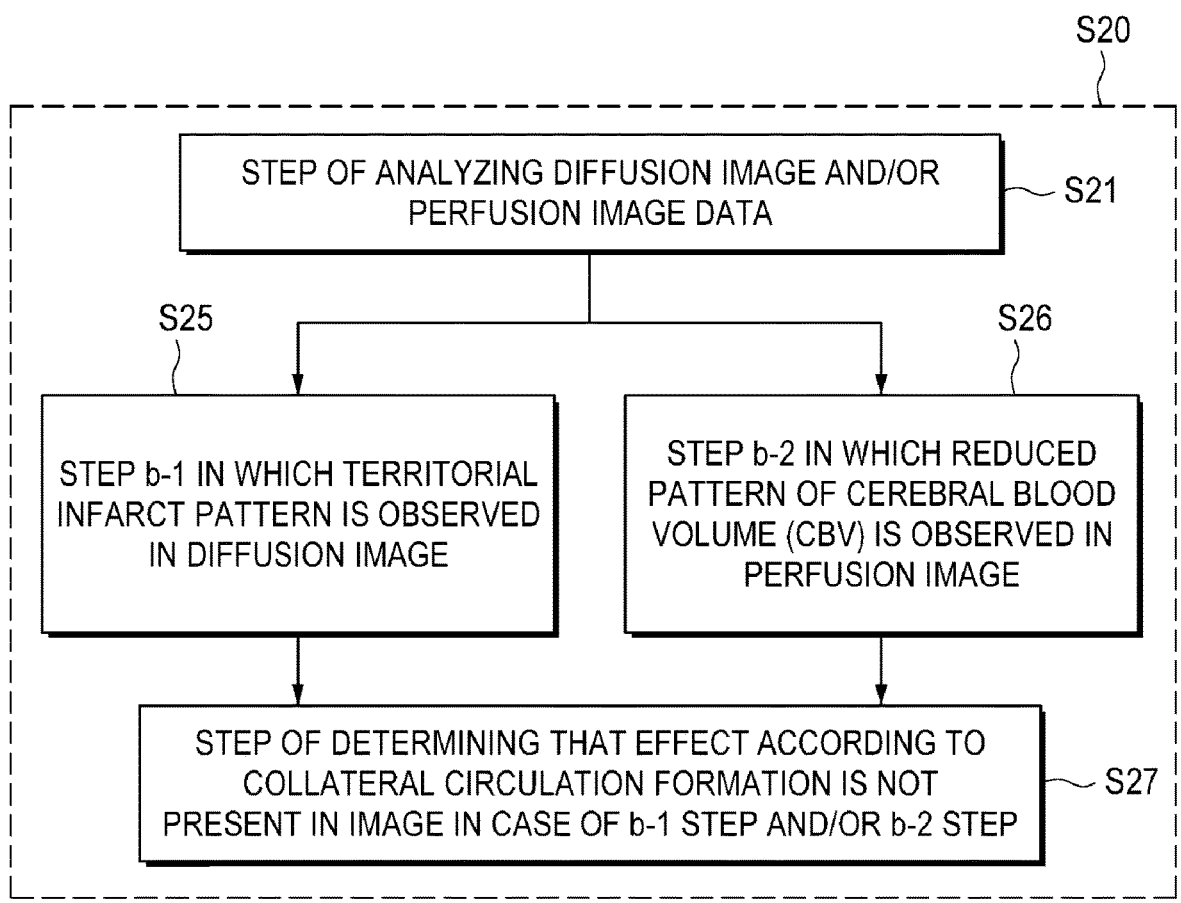
FIG. 6 is a flowchart for explaining a process of classifying a type of occlusion to embolism because the effect according to collateral circulation formation in the vicinity of the occluded large vessel is not present in a medical image, with regard to FIG. 4.

FIG. 6 is a flowchart for explaining a process of classifying a type of occlusion to embolism because the effect according to collateral circulation formation in the vicinity of the occluded large vessel is not present in a medical image, with regard to FIG. 4.

Referring to FIG. 6, the ICAS/embolism determining unit 31 may distinguish embolism from ICAS based on perfusion image information and diffusion image information (S21).

As described above, the embolism is a state in which a normal blood vessel is blocked by blood clots so that collateral circulation in the vicinity of position of the embolism is not developed. In the case of the embolism, a step b-1 in which a territorial infarct pattern appears in the diffusion image may be observed (S25).

Further, a step b-2 in which a reduction of the cerebral blood volume (CBV) appears in the perfusion image may be observed (S26).

Accordingly, when the step b-1 in which a territorial infarct pattern appears in the diffusion image and/or the step b-2 in which a reduction of the cerebral blood volume (CBV) appears in the perfusion image are observed, the ICAS/embolism determining unit 31 determines that the effect according to the collateral circulation formation is not present in the image (S27) and may determine embolism based thereon (S32).

In the meantime, the ICAS/embolism determining unit 31 applies an artificial intelligence classification model to configure a 3D convolutional neural network (CNN) architecture with inception-V1 as a base network, learn a feature for voxel data of brain diffusion image and the perfusion image, and classify the cause of the large vessel occlusion (LVO) in detail based thereon.

Figure 7:
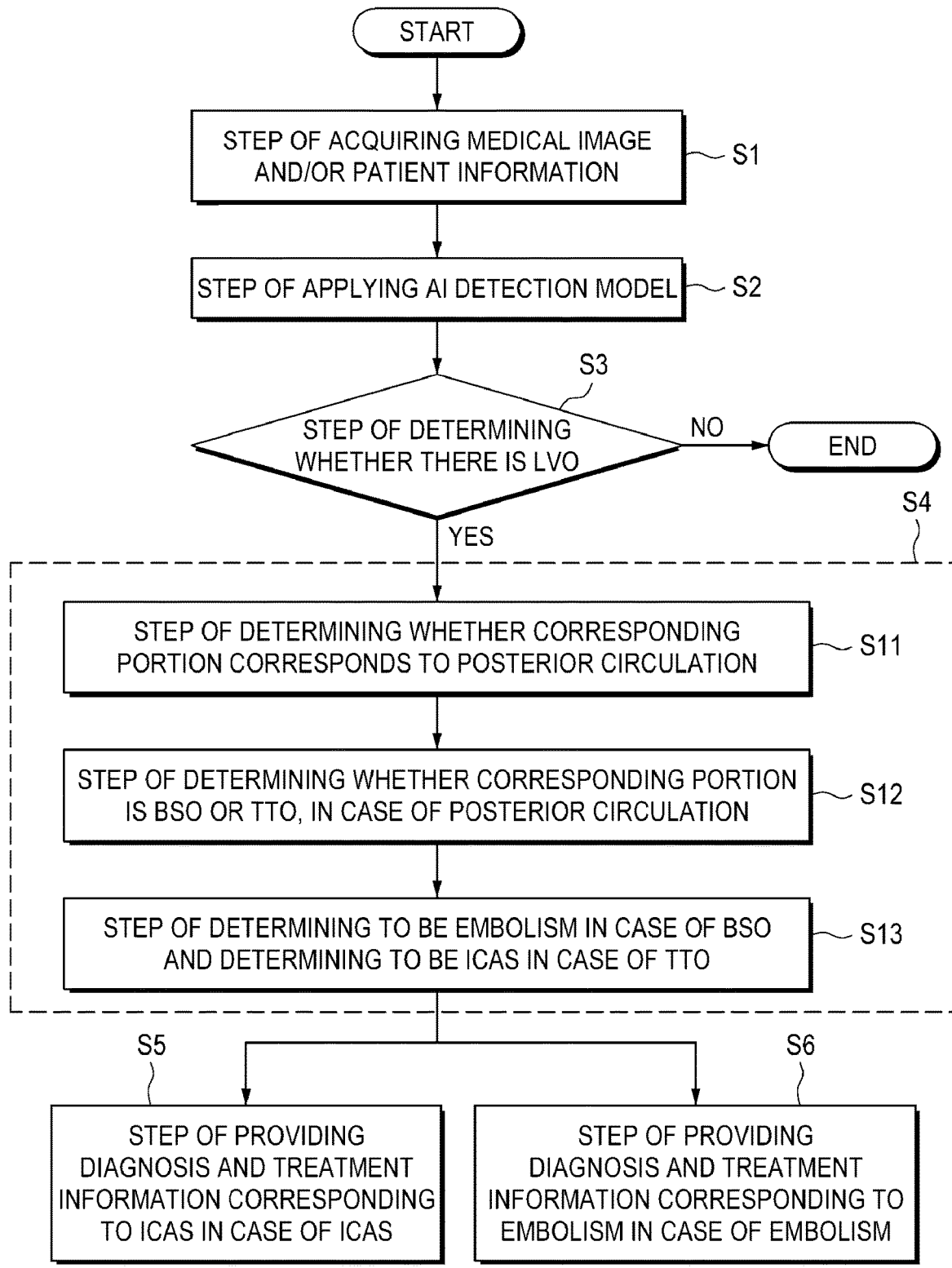
FIG. 7 is a flowchart for explaining a method for classifying the type of generated large vessel occlusion by identifying whether a corresponding part is BSO or TTO when the position of the occluded large vessel corresponds to PC.

Method for Classifying Type of Large Vessel Occlusion by Identifying Whether Corresponding Part is BSO or TTO when Position of Occluded Large Vessel Corresponds to PC FIG. 7 is a flowchart for explaining a method for classifying the type of generated large vessel occlusion by identifying whether a corresponding part is BSO or TTO when the position of the occluded large vessel corresponds to PC.

Referring to FIG. 7, when the position of the occluded large vessel corresponds to posterior circulation (PC), the ICAS/Embolism determining unit 31 may classify a type of the generated large vessel occlusion by identifying whether a corresponding part is branching site occlusion (BSO) or truncal type occlusion (TTO).

When the position of the occluded large vessel corresponds to posterior circulation (PC), in most patients, embolism appears when the position is a branching site occlusion (BSO) position and ICAS appears when the position is a truncal type occlusion (TTO) position.

Specifically, the combination of BSO-embolism and TTO-ICAS is more obvious in the East.

Accordingly, when the position of the occluded large vessel corresponds to posterior circulation (PC) (S11), it is possible to easily distinguish embolism from ICAS based on whether a position of the corresponding portion is BSO or TTO (S13).

To this end, the AC/PC determining unit 32 may determine whether the position of the occluded large vessel corresponds to posterior circulation (PC) or an anterior circulation (AC).

Further, the BSO/TTO determining unit 33 may provide a function of determining whether the corresponding portion is branching site occlusion (BSO) or truncal type occlusion (TTO).

Method for Classifying Type of Generated Large Vessel Occlusion Using BSO/TTO Information, Collateral Circulation Formation Information, and Physical Information of Patient Together when Position of Occluded Large Vessel Corresponds to AC In the meantime, when the position of the occluded large vessel corresponds to anterior circulation (AC), similarly to the posterior circulation (PC), in most patients, embolism appears when the position is a branching site occlusion (BSO) position and ICAS appears when the position is a truncal type occlusion (TTO) position.

However, BSO-embolism and TTO-ICAS probability of the anterior circulation (AC) is determined to be lower than that of the posterior circulation (PC) so that the type of large vessel occlusion needs to be classified using additional information.

Figure 8:
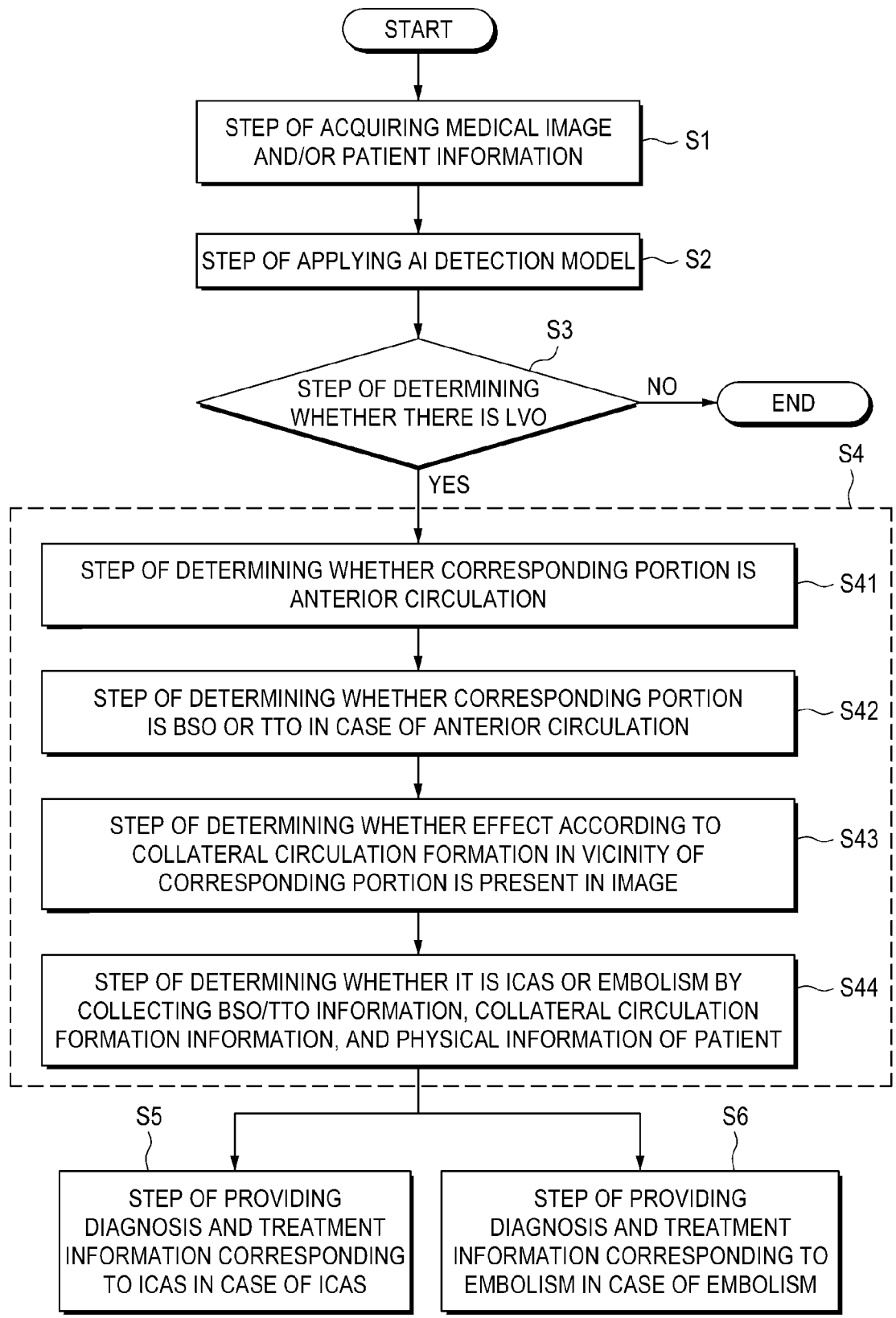
FIG. 8 is a flowchart for explaining a method for classifying the type of generated large vessel occlusion using BSO/TTO information, collateral circulation formation information, and physical information of the patient together when the position of the occluded large vessel corresponds to anterior circulation (AC).

FIG. 8 is a flowchart for explaining a method for classifying the type of generated large vessel occlusion using BSO/TTO information, collateral circulation formation information, and physical information of the patient together when the position of the occluded large vessel corresponds to anterior circulation (AC).

Referring to FIG. 8, when the position of the occluded large vessel corresponds to anterior circulation (AC) (S41), the ICAS/embolism determining unit 31 determines whether the corresponding portion is BSO or TTO (S42) and determines whether the effect according to the collateral circulation formation in the vicinity of the portion is in the image (S43).

Thereafter, the ICAS/embolism determining unit 31 may classify the type of the generated large vessel occlusion using physical information of the patient acquired in the step S1, BSO/TTO information acquired in the step S42, and collateral circulation formation information acquired in the step S43 together (S44).

That is, it is possible to determine whether the type of the generated large vessel occlusion is embolism or ICAS by assigning a first additional point to physical information which varies depending on embolism and ICAS, assigning a second additional point to a BSO-embolism and TTO-ICAS probability, and assigning a third additional point to increase the ICAS probability when the effect according to the collateral circulation formation is present in the image, as described with reference to FIGS. 4 to 6, and comprehensively using the first additional point, the second additional point, and third additional point.

Method for Supporting Health Care Provider to Determine Treatment Direction Appropriate for Patient when Type of Large Vessel Occlusion is Embolism The diagnosing unit 40 may provide information for supporting health care providers to determine a treatment direction appropriate for the patient differently in a case in which the type of the generated large vessel occlusion is embolism and a case in which the type of the generated large vessel occlusion is ICAS. When the type of the generated large vessel occlusion is embolism, the embolism diagnosing unit 42 may provide diagnosis and treatment information corresponding to embolism to the health care provider.

First, a process of determining whether the patient determined to have embolism is mild or serious by the embolism diagnosing unit 42 is performed.

In the case of a mild patient, the embolism diagnosing unit 42 may recommend a treatment direction using a thrombolytic agent to the health care provider.

Further, in the case of a serious patient, the embolism diagnosing unit 42 may recommend a treatment direction using a thrombectomy to the health care provider.

Further, when the type of the generated large vessel occlusion is embolism and the blood clots are removed, the most treatment may be completed. Therefore, even though the blood clots are not satisfactorily removed, more aggressive surgical measures may be attempted to additionally remove the blood clots by taking time.

In contrast, even after removing the blood clots, additional treatment for ICAS is necessary and the blood clots are not satisfactorily removed due to arteriosclerosis, which may cause a problem that the blood vessel is torn. Therefore, as compared with the embolism, it is necessary to refrain from aggressive removal measures.

Thereafter, the information provided by the embolism diagnosing unit 42 may be transmitted to external institution such as a hospital related to the patient, based on wired/wireless communication.

Even though it is not illustrated, information transmission to the external institution (a tertiary referral hospital) may be performed by a communication unit and the communication unit may transmit corresponding information to a predetermined outside (for example, a hospital) by wired communication, short-distance communication, or long-distance communication.

Method for Supporting Health Care Provider to Determine Treatment Direction Appropriate for Patient when Type of Large Vessel Occlusion is ICAS Currently, primarily, a treatment using a thrombolytic agent which is a drug treatment agent which dissolves clots formed by the blood coagulation is tried or a treatment by thrombectomy is performed, within three hours to four and half hours from the time when the occlusion occurs, without identifying whether the large vessel occlusion of the patient is Embolism or ICAS. However, in the case of the ICAS, when the treatment using the thrombolytic agent is performed, platelets are more coagulated in the body so that it is difficult to perform treatment using antiplatelet agents for hours. Therefore, there may be a problem in that the primarily performed thrombolytic treatment may deteriorate the condition.

Further, in the case of the embolism, when the blood clots are removed by the thrombectomy, the problems are solved. In contrast, in the case of the ICAS, even after removing the blood clots, stenosis due to arteriosclerosis still remains so that follow-up treatment is required. However, it is difficult for the health care providers to identify the form of large vessel occlusion in advance before the surgery and it is impossible to find out the corresponding situation and the necessity of the follow-up treatment after performing the surgery.

Accordingly, the ICAS diagnosing unit 41 and the embolism diagnosing unit 42 provide information for supporting the health care provider to determine a treatment direction appropriate for the patient differently in a case in which the type of the generated large vessel occlusion is embolism and a case in which the type of the generated large vessel occlusion is ICAS to solve the above-mentioned problems.

When the type of the generated large vessel occlusion is ICAS, unlike the embolism diagnosing unit 42, the ICAS diagnosing unit 42 may primarily recommend a treatment using percutaneous transluminal angioplasty and/or a treatment direction using an antiplatelet agent to the health care provider.

When such a primary treatment does not show a great effect, the ICAS diagnosing unit 41 may secondarily recommend a treatment using a thrombolytic agent and/or a treatment direction using a thrombectomy to the health care provider.

In addition, unlike the embolism, in the ICAS, various secondary treatments may be applied.

As a drug treatment, as a therapeutic drug, in addition to an antiplatelet agent, sympathetic drugs or statins may be used.

Next, a secondary treatment using stent may be applied. A treatment using stent may be applied as an alternative to overcome the limitation of the drug treatment which is used as a primary treatment method.

As the other therapies, a treatment using a mechanism which increases blood flow going up by blocking blood vessel going down by inserting a balloon into a descending aorta or a counterpulsation treatment which is consistently repeatedly performed by tying a band to a lower extremities and instantaneously tightens to allow the blood flow to be directed to the brain may also be additionally used.

Thereafter, the information provided by the ICAS diagnosing unit 41 may be transmitted to external institution such as a hospital related to the patient, based on wired/wireless communication.

Even though it is not illustrated, information transmission to the external institution (a tertiary referral hospital) may be performed by a communication unit and the communication unit may transmit corresponding information to a predetermined outside (for example, a hospital) by wired communication, short-distance communication, or long-distance communication.

Effect According to Present Disclosure

The present disclosure provides a method, an apparatus, and a system for detecting and classifying ischemic stroke based on medical images to solve the above-described problems of the related art.

Specifically, the present disclosure may provide a method, an apparatus, and a system for detecting a position of an occluded large vessel and classifying a type of the generated large vessel occlusion based on medical images acquired from a suspected ischemic stroke patient due to the large vessel occlusion and patient information to calculate and provide information for supporting health care providers to determine a treatment direction suitable for a patient.

Further, the present disclosure may provide a method, an apparatus, and a system for classifying a type of the generated large vessel occlusion by determining whether an effect according to collateral circulation formation in the vicinity of the occluded large vessel is present in the medical image.

Further, the present disclosure may provide a method, an apparatus, and a system for classifying a type of the generated large vessel occlusion by identifying whether a corresponding part is branching site occlusion (BSO) or truncal type occlusion (TTO) when the position of the occluded large vessel corresponds to posterior circulation (PC).

Further, the present disclosure may provide a method, an apparatus, and a system for classifying a type of the generated large vessel occlusion using information indicating that the corresponding part is branching site occlusion (BSO)/truncal type occlusion (TTO) information, collateral circulation formation information, and physical information of the patient together when the position of the occluded large vessel corresponds to anterior circulation (AC).

Further, the present disclosure may provide a method, an apparatus, and a system for supporting health care providers to identify a type of the large vessel occlusion before the surgery in advance and determining a treatment direction appropriate for the patient by identifying whether the type of the generated large vessel occlusion is embolism or ICAS.

In the meantime, a technical object to be achieved in the present disclosure is not limited to the aforementioned effects, and another not-mentioned effects will be obviously understood by those skilled in the art from the description below.

The above-described exemplary embodiments of the present disclosure may be implemented through various methods. For example, the exemplary embodiments of the present disclosure may be implemented by a hardware, a firmware, a software, and a combination thereof.

When the exemplary embodiment is implemented by the hardware, the method according to the exemplary embodiment of the present disclosure may be implemented by one or more application specific integrated circuits (ASICs), digital signal processors (DSPs), digital signal processing devices (DSPDs), programmable logic devices (PLDs), field programmable gate arrays (FPGAs), a processor, a controller, a microcontroller, a microprocessor, or the like.

When the exemplary embodiment is implemented by the firmware or the software, the method according to the exemplary embodiment of the present disclosure may be implemented by a module, a procedure, or a function which performs a function or operations described above. The software code is stored in the memory unit to be driven by the processor. The memory unit is located inside or outside the processor and may exchange data with the processor, by various known units.

As described above, the detailed description of the exemplary embodiments of the disclosed present disclosure is provided such that those skilled in the art implement and carry out the present disclosure. While the present disclosure has been described with reference to the preferred embodiments, it will be understood by those skilled in the art that various changes and modifications of the present disclosure may be made without departing from the spirit and scope of the present disclosure. For example, those skilled in the art may use configurations disclosed in the above-described exemplary embodiments by combining them with each other. Therefore, the present disclosure is not intended to be limited to the above-described exemplary embodiments but to assign the widest scope consistent with disclosed principles and novel features.

The present disclosure may be implemented in another specific form within the scope without departing from the spirit and essential feature of the present disclosure. Therefore, the detailed description should not limitatively be analyzed in all aspects and should be exemplarily considered. The scope of the present disclosure should be determined by rational interpretation of the appended claims and all changes are included in the scope of the present disclosure within the equivalent scope of the present disclosure. The present disclosure is not intended to be limited to the above-described exemplary embodiments but to assign the widest scope consistent with disclosed principles and novel features. Further, claims having no clear quoting relation in the claims are combined to configure the embodiment or may be included as new claims by correction after application.

What is claimed is:

1. A medical image-based ischemic stroke detecting, classifying, and treatment method, comprising:
   a first step of collecting images of a brain of a patient, by an acquiring unit;
   a second step of determining, by a detecting unit, that the patient has a large vessel occlusion, based on the collected images;
   a third step of determining whether a type of the large vessel occlusion of the patient is embolism or intracranial atherosclerosis (ICAS), by a determining unit;
   a fourth step of providing treatment direction information based on the determined type of the large vessel occlusion, by a diagnosing unit; and
   a fifth step of providing a treatment selected from an angioplasty, an antiplatelet agent treatment, a thrombolytic agent treatment, a thrombectomy, a treatment using a drug other than the antiplatelet agent, a treatment using a stent, a treatment using insertion of a balloon, a counterpulsation treatment, or a combination thereof,
   wherein the second step includes:
   a step 2-1 of performing spatial alignment of the collected images of the brain for spatial normalization and extracting a region of interest from the spatial normalized images, by an image processing unit; and
   a step 2-2 of receiving the region of interest from the image processing unit and determining the presence or absence of large vessel occlusion, by a large vessel occlusion detecting unit; and
   wherein the third step includes:
   a step 3-1 of determining whether a position of the large vessel occlusion corresponds to posterior circulation (PC) or anterior circulation (AC), by the determining unit;
   a step 3-2 of determining whether a type of the large vessel occlusion is branching-site occlusion (BSO) or truncal-type occlusion (TTO), by the determining unit, and
   a step 3-3 of determining a type of the large vessel occlusion based on first determination for the posterior circulation (PC) or the anterior circulation (AC) and second determination of the BSO or the TTO, by the determining unit.

2. The method according to claim 1, wherein in the first step, the acquiring unit collects an angiography image of the brain of the patient, and wherein in the second step, the determination that the patient has a large vessel occlusion, by the detection unit, employs voxel information of the angiography image.

3. The method according to claim 2, wherein in the second step, the determination that the patient has a large vessel occlusion uses an artificial intelligence model architecture which is configured by combining a recurrent neural network (RNN) layer for considering a serial slice of the patient in the angiography image and a convolutional neural network (CNN) layer for extracting a feature in the angiography image.

4. The method according to claim 1, wherein in the first step, the acquiring unit collects a perfusion image and a diffusion image of the brain of the patient so as to make it possible to observe collateral circulation development in a vicinity of a blood vessel where arteriosclerosis progresses, and wherein in the third step, the determining unit determines whether to observe a first event of collateral circulation development using at least one of the perfusion image and the diffusion image.

5. The method according to claim 4, wherein when the first event of collateral circulation development is observed, the determining unit determines the type of the large vessel occlusion as ICAS.

6. The method according to claim 4, wherein when at least one of a first condition in which a difference between an infarct core volume and a volume of a surrounding cortex region is equal to or higher than a predetermined value in the perfusion image and a second condition in which an infarct pattern appears as a scattered pattern or a border zone infarct pattern in the diffusion image is satisfied, in the third step, the determining unit determines that the first event is observed and determines the type of the large vessel occlusion as ICAS.

7. The method according to claim 4, wherein when at least one of a first condition in which a cerebral blood volume (CBV) is reduced in the perfusion image and a second condition in which the infarct pattern is a territorial infarct pattern in the diffusion image is satisfied, in the third step, the determining unit determines that the first event is not observed and determines the type of the large vessel occlusion as embolism.

8. The method according to claim 1, wherein when the position of the large vessel occlusion is located in the PC, in the step 3-3, if the type of the large vessel occlusion is the BSO, the determining unit determines the large vessel occlusion to be embolism and if the type of the large vessel occlusion is the TTO, the determining unit determines the large vessel occlusion to be ICAS.

9. The method according to claim 1, wherein when the position of the large vessel occlusion is located in the AC, in the first step, the acquiring unit additionally collects physical information of the patient, and in the step 3-2, the determining unit additionally determines whether a first event in which collateral circulation is developed is observed, and in the step 3-3, the determining unit determines a type of the large vessel occlusion using the physical information, information indicating whether the first event is observed, and information indicating whether the type of the large vessel occlusion is the BSO or TTO together.

10. The method according to claim 1, wherein when the determined type of the large vessel occlusion is the ICAS, the fourth step includes:
    a step 4-1 of primarily providing at least one of treatment direction information for using the angioplasty or treatment direction information for using the antiplatelet agent, by the diagnosing unit; and
    a step 4-2 of, when an additional treatment is necessary for the patient, secondarily providing treatment direction information containing the thrombolytic agent treatment, the thrombectomy, the treatment using the drug other than the antiplatelet agent, the treatment using the stent, the treatment using insertion of the balloon, the counterpulsation treatment, or a combination thereof, by the diagnosing unit.

11. The method according to claim 1, further comprising:
    sixth step of, when the patient has received the thrombectomy treatment, after a predetermined time from the thrombectomy treatment, outputting information proposing to stop the thrombectomy treatment.

12. The method according to claim 1, wherein when the determined type of the large vessel occlusion is the embolism, the fourth step includes:
   a step 4-1 of determining whether the patient has a mild embolism or a serious embolism, by the diagnosing unit; and
   a step 4-2 of providing treatment direction information for the thrombolytic agent treatment for the mild embolism and providing treatment direction information for the thrombectomy treatment for the serious embolism, by the diagnosing unit.

13. The method according to claim 1,
   wherein the fourth step further comprising a step of transmitting the treatment direction information provided by the diagnosing unit to a predetermined institution based on at least one of wired communication or wireless communication.

* * * * *